United States Patent [19]

Collins et al.

[11] Patent Number: 5,763,727
[45] Date of Patent: Jun. 9, 1998

[54] FLUIDIZED BED PARAFFIN DISPROPORTIONATION

[75] Inventors: Nick A. Collins, Medford, N.J.; Mohsen N. Harandi, Langhorne, Pa.

[73] Assignee: Mobil Oil Corporation, Fairfax, Va.

[21] Appl. No.: 11,573

[22] Filed: Feb. 1, 1993

[51] Int. Cl.$^6$ ............................................. C07C 6/08
[52] U.S. Cl. ............................................. 585/708
[58] Field of Search ................................. 585/708

[56] References Cited

U.S. PATENT DOCUMENTS

| | | | |
|---|---|---|---|
| Re. 28,341 | 2/1975 | Wadlinger et al. | 208/120 |
| 3,308,069 | 3/1967 | Wadlinger et al. | 252/455 |
| 3,354,078 | 11/1967 | Miale et al. | 208/120 |
| 3,702,886 | 11/1972 | Argauer et al. | 423/328 |
| 3,760,024 | 9/1973 | Cattanach | 260/673 |
| 3,812,199 | 5/1974 | Chen et al. | 260/676 R |
| 3,953,537 | 4/1976 | Chloupek | 585/708 |
| 4,528,412 | 7/1985 | Steacy | 585/415 |
| 4,565,897 | 1/1986 | Gane et al. | 585/415 |
| 4,590,323 | 5/1986 | Chu | 585/417 |
| 4,613,716 | 9/1986 | McNiff | 585/415 |
| 4,642,404 | 2/1987 | Shihabi | 585/415 |
| 4,665,265 | 5/1987 | Chu et al. | 585/533 |
| 4,686,316 | 8/1987 | Morrison | 585/708 |
| 4,754,100 | 6/1988 | Sorensen et al. | 585/708 |
| 4,827,069 | 5/1989 | Kushnerick et al. | 585/415 |
| 4,990,710 | 2/1991 | Dessau et al. | 585/277 |
| 5,171,912 | 12/1992 | Harandi | 585/301 |

*Primary Examiner*—Ponnathapura Achutamurthy
*Attorney, Agent, or Firm*—Thomas W. Steinberg; Malcolm D. Keen

[57] ABSTRACT

A process is provided for the disproportionation of $C_3$–$C_5$ paraffins. Propane, butanes and/or pentanes are reacted over a zeolite catalyst having a low acid activity in a turbulent fluidized bed reactor regenerator system operating at low to moderate pressures.

20 Claims, No Drawings

FLUIDIZED BED PARAFFIN DISPROPORTIONATION

FIELD OF THE INVENTION

This application is directed to a fluidized bed process to disproportionate paraffins over low acidity zeolite catalysts.

BACKGROUND OF THE INVENTION

Current environmental legislation mandating reductions in Reid vapor pressure (RVP) for gasoline has resulted in interest in converting light end streams, i.e., butanes and pentanes, to high octane, low RVP fuels. Partial conversion of these butanes to lower RVP $C_5+$ product can return some of butane material to the gasoline pool. Conversion of pentanes to butanes and $C_6+$ produces alkylation feedstock and removes high RVP pentanes from gasoline. Also, in some refinery schemes, propane has higher value than butane making butane disproportionation attractive.

U.S. Pat. No. 3,760,024 describes the conversion of $C_2$–$C_4$ paraffins, olefins and mixtures thereof over a zeolite having the structure of ZSM-5 to form aromatic hydrocarbons. U.S. Pat. No. 3,812,199 describes disproportionation of paraffin hydrocarbons with a zeolite, preferably dealuminized mordenite. U.S. Pat. No. 4,528,412 describes making aromatic hydrocarbons by reacting $C_3$ or $C_4$ paraffins or olefins over a zeolite catalyst. U.S. Pat. No. 4,590,323 describes a process for producing aromatics from paraffins with a zeolite catalyst with an oxide modifier. U.S. Pat. Nos. 4,565,897 and 4,613,716 describe the conversion of $C_3$–$C_4$ hydrocarbons mixed with $C_2$ hydrocarbons by contact with MFI-type zeolites (stated to include ZSM-5), to form aromatic hydrocarbons.

U.S. Pat. Nos. 4,686,316 and 4,754,100 describe the conversion of propane to butanes over high acid activity zeolites. U.S. Pat. Nos. 4,642,404 and 4,665,265 describe the conversion of feedstock comprising $C_2+$ olefins, $C_2$–$C_7$ paraffins or a mixture thereof over a catalyst having enhanced acid activity.

Therefore, it is an object of the present invention to disproportionate paraffins using a low Alpha Value zeolite catalyst. It is a further object of the present invention to disproportionate paraffins in a low pressure, turbulent fluidized bed.

SUMMARY OF THE INVENTION

The present invention provides a fluidized bed process for the disproportionation of paraffins. The process of the present invention is operated at high temperature, low pressure and low catalyst activity, as measured by Alpha Value.

The invention therefore includes a process for the disproportionation of a feedstock comprising $C_3$–$C_5$ paraffins comprising reacting the paraffins in a turbulent fluidized bed reactor at a pressure less than about 300 psig with a catalyst composition comprising a crystalline aluminosilicate zeolite having an Alpha Value below about 10.

DETAILED DESCRIPTION

In the process of the present invention propane, butanes and/or pentanes are reacted over a zeolite catalyst in a fluidized bed reactor operating at low to moderate pressure. The feed paraffins disproportionate to form a product rich in paraffins with carbon numbers one less and one greater than the feed. For example, butane disproportionates primarily to propane and pentanes.

The process of the present invention uses a fluidized catalyst bed in a vertical reactor column having a turbulent reaction zone by passing feedstock gas upwardly through the reaction zone at a velocity greater than dense bed transition velocity in a turbulent regime and less than transport velocity for the average catalyst particle and withdrawing a portion of coked catalyst from the reaction zone, oxidatively regenerating the withdrawn catalyst, and returning regenerated catalyst to the reaction zone at a rate to control catalyst activity.

The fluidized bed reactor involves a rapid movement of the solid catalytic particles throughout the bed so that the operation can come close to one of uniform temperature throughout the reactor. The fluidized bed reactor allows catalyst to be regenerated while the unit is in operation by continuously removing a portion of the catalyst from the reactor for regeneration treatment and subsequent flow back into the reactor. Auxiliary units, such as cyclone separators or dust collectors may be provided for separating out the solid particles or catalyst fines from the product stream.

Particle size distribution can be a significant factor in achieving overall homogeneity in turbulent regime fluidization.

It is desired to operate the process with particles that will mix well throughout the bed. Large particles having a particle size greater than 250 microns should be avoided, and it is advantageous to employ a particle size range consisting essentially of 1 to 150 microns. Average particle size is usually about 20 to 100 microns, preferably 40 to 80 microns. Particle distribution may be enhanced by having a mixture of larger and smaller particles within the operative range, and it is particularly desirable to have a significant amount of fines. Close control of distribution can be maintained to keep about 10 to 25 wt. % of the total catalyst in the reaction zone in the size range less than 32 microns. This class of fluidizable particles is classified as Geldart Group A. Accordingly, the turbulent fluidization regime is controlled to assure operation between the transition velocity and transport velocity. Fluidization conditions are substantially different from those found in non-turbulent dense beds or transport beds.

Under optimized process conditions the turbulent bed has a superficial vapor velocity of about 0.3 to 2 meters per second (m/sec). At higher velocities entrainment of fine particles may become excessive, and beyond about 3 m/sec the entire bed may be transported out of the reaction zone. At lower velocities, the formation of large bubbles or gas voids can be detrimental to conversion. Even fine particles cannot be maintained effectively in a turbulent bed below about 0.1 m/sec.

A convenient measure of turbulent fluidization is the bed density. A typical turbulent bed has an operating density of about 100 to 500 kg/m³, preferably about 300 to 500 kg/m³, measured at the bottom of the reaction zone, becoming less dense toward the top of the reaction zone, due to pressure drop and particle size differentiation. This density is generally between the catalyst concentration employed in dense beds and the dispersed transport systems. Pressure differential between two vertically spaced points in the reactor column can be measured to obtain the average bed density at such portion of the reaction zone. For instance, in a fluidized bed system employing low Alpha Value ZSM-5 particles having an apparent packed density of 750 kg/m³ and real density of 2430 kg/m³, an average fluidized bed density of about 300 to 500 kg/m³ is satisfactory.

By virtue of the turbulence experienced in the turbulent regime, gas-solid contact in the catalytic reactor is improved, providing substantially complete conversion, enhanced selectivity, and temperature uniformity. One main advantage of this technique is the inherent control of bubble size and characteristic bubble lifetime. Bubbles of the gaseous reaction mixture are small, random, and short-lived, thus resulting in good contact between the gaseous reactants and the solid catalyst particles.

The process of the present invention may be used to convert high Reid vapor pressure (RVP) butane streams to products rich in propane for use as LPG and a $C_5+$ gasoline with lower RVP than the feed butanes. In general, the preferred feed for the present invention contains at least about 90 wt % butanes. Suitable sources for the butane feed include paraffinic refinery streams such as the off-gases from a catalytic reformer or from a hydrocracker and the n-butane rich stream discharged from the isobutanizer tower of an alkylation plant.

The process of the present invention may also be used to convert pentanes. If pentanes are undesirable due to their relatively high RVP they may be converted primarily to butanes useful as alkylation or dehydrogenation feedstocks and a lower RVP $C_5+$ gasoline. Suitable feeds include saturated gas plant $C_5$'s, TAME raffinate and skeletal isomerization by-product.

The process is also especially useful for converting propane. In general, the propane content of the feed is at least about 95%. Suitable sources for the propane feed include petroleum refinery streams and natural gas liquids.

Low pressure operation is desirable for reducing vessel costs. The process of the present invention operates at a pressure of less than about 300 psig and preferably at a pressure less than about 200 psig.

The process of the present invention operates at high temperature. Generally the process operates at a temperature in the range of about 750° to about 1000° F. and preferably at a temperature in the range of about 850° to about 950° F. The process of the present invention generally operates at a WHSV of about 0.1 to about 5.0 $hr^{-1}$ and preferably at a WHSV of about 0.2 to about 2.0 $hr^{-1}$.

By using higher temperatures at lower pressures higher feed paraffin conversions and improved product selectivities are obtained with low Alpha Value catalysts.

Fluidized bed operation enables continuous catalyst regeneration which permits the use of less stable zeolites than in fixed bed processes.

The catalysts useful in the process of this invention contain a zeolite having a low acid activity. Acidic activity is related to the number of sites available for protonation and removal of aluminum reduces the proportion of these sites. As is known in the art and used in the specification, the acidity of the catalyst may be measured by its Alpha Value.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of silica-alumina cracking catalyst taken as an Alpha of 1 (Rate Constant=0.016 $sec^{-1}$). The Alpha Test is described in U.S. Pat. No. 3,354,078; in the *Journal of Catalysis*, 4, 527 (1965); 6, 278 (1966); and 61, 395 (1980), each incorporated herein by reference as to that description. The experimental conditions of the test used herein include a constant temperature of 538° C. and a variable flow rate as described in detail in the *Journal of Catalysis*, 61, 395.

The desired low Alpha Value zeolites may be prepared by direct synthesis or converted into the desired low Alpha Value form by various conventional techniques, such as steaming, cation exchange, calcination and acid treatment.

Zeolites useful in the present invention have a low Alpha Value, preferably below about 10 and more preferably below about 5. Preferred catalysts include ZSM-5, zeolite Beta and a mixture. of Pt-Sn/ZSM-5 and ZSM-5.

Zeolite Beta is described in U.S. Pat. Nos. 3,308,069 and Re. No. 28,341, incorporated herein by reference.

ZSM-5 is described in U.S. Pat. No. 3,702,886, incorporated herein by reference. A preferred ZSM-5 is Pt-Sn/ZSM-5 described in U.S. Pat. No. 4,990,710, incorporated herein by reference.

It may be desirable to incorporate the zeolite with another material resistant to the temperature and other conditions employed in the process. Such matrix materials include synthetic or natural substances as well as inorganic materials such as clay, silica and/or metal oxides, such as titania or zirconia. The latter may be either naturally occurring or in the form of gelatinous precipitates or gels including mixtures of silica and metal oxides. Naturally occurring clays which can be composited with the zeolite include those of the montmorillonite and kaolin families. These clays can be used in the raw state as originally mined or initially subjected to calcination, acid treatment or chemical modification. These materials, i.e., clays, oxides, etc., function, in part, as binders for the catalyst.

In addition to the foregoing materials, the zeolites may be composited with a porous matrix material, such as alumina, silica-alumina, silica-magnesia, silica-zirconia, silica-thoria, silica-beryllia, silica-titania as well as ternary compositions, such as silica-alumina-thoria, silica-alumina-zirconia, silica-alumina-magnesia, and silica-magnesia-zirconia. The matrix may be in the form of a cogel. The relative proportions of zeolite component and inorganic oxide gel matrix may vary widely with the zeolite content ranging from between 1 to 99, more usually 5 to 80, percent by weight of the composite.

The following examples illustrate the process of the present invention.

Example 1

In this example normal butane is disproportionated in a fluidized bed reactor at a temperature of 900° F., a pressure of 150 psig and a space velocity of 0.75 $hr^{-1}$ over a ZSM-5 catalyst. The ZSM-5 catalyst is prepared in accordance with U.S. Pat. No. 3,702,886, incorporated herein by reference and has an Alpha Value of 5.

Example 2

In this example isobutane is disproportionated in a fluidized bed reactor at a temperature of 900° F., a pressure of 150 psig and a space velocity of 0.75 $hr^{-1}$ over a ZSM-5 catalyst. The ZSM-5 catalyst is prepared in accordance with U.S. Pat. No. 3,702,886, incorporated herein by reference and has an Alpha Value of 5.

Example 3

In this example isobutane is disproportionated in a fluidized bed reactor at a temperature of 900° F., a pressure of 150 psig and a space velocity of 1.5 $hr^{-1}$ over a ZSM-5 catalyst. The ZSM-5 catalyst is prepared in accordance with U.S. Pat. No. 3,702,886, incorporated herein by reference and has an Alpha Value of 5.

Butane conversion and product selectivities for Examples 1, 2 and 3 are shown in Table 1.

TABLE 1

|  | Example 1 | Example 2 | Example 3 |
|---|---|---|---|
| Operating conditions | | | |
| Temperature, °F. | 900 | 900 | 900 |
| Pressure, psig | 150 | 150 | 150 |
| Butane WHSV, $hr^{-1}$ | 0.75 | 0.75 | 1.50 |
| Butane feed | n-Butane | Isobutane | Isobutane |
| Butane conversion, % | 60 | 32 | 6 |
| Product Selectivities, wt. % | | | |
| $C_2-$ | 12.4 | 4.7 | 5.8 |
| Propane | 55.7 | 50.8 | 36.5 |
| Propene | 2.3 | 1.6 | 5.3 |
| n-Butane | — | 20.0 | 24.9 |
| Isobutane | 10.0 | — | — |
| Butenes | 2.9 | 2.1 | 6.4 |
| n-Pentane | 2.9 | 4.4 | 5.4 |
| Isopentane | 2.7 | 10.4 | 10.1 |
| Pentenes | 1.5 | 1.0 | 2.3 |
| $C_6+$ | 9.8 | 5.1 | 3.4 |

Changes and modifications in the specifically described embodiments can be carried out without departing from the scope of the invention which is intended to be limited only by the scope of the appended claims.

We claim:

1. A process for the disproportionation of a feedstock comprising $C_3$–$C_5$ paraffins comprising reacting the paraffins in a fluidized bed reactor at a pressure less than about 300 psig with, a catalyst composition comprising a crystalline aluminosilicate zeolite having an Alpha Value below about 10.

2. The process of claim 1 wherein said pressure is less than about 200 psig.

3. The process according to claim 1 wherein the fluidized bed reactor is operated under turbulent conditions at a superficial vapor velocity in the range of about 0.3 to about 2 meters per second.

4. The process according to claim 1 wherein the catalyst is continuously regenerated.

5. The process according to claim 1 wherein said Alpha Value is below about 5.

6. The process according to claim 1 wherein said paraffins comprise propane.

7. The process according to claim 1 wherein said paraffins comprise butanes.

8. The process according to claim 7 wherein said paraffins comprise normal butane.

9. The process according to claim 1 wherein said paraffins comprise pentanes.

10. The process according to claim 1 wherein said process operates at a temperature in the range of from about 750° to about 1000° F.

11. The process according to claim 1 wherein said zeolite has the structure of zeolite Beta.

12. The process according to claim 1 wherein said zeolite has the structure of ZSM-5.

13. The process of claim 12 wherein said zeolite having the structure of ZSM-5 is Pt-Sn/ZSM-5.

14. A process for the disproportionation of a feedstock comprising butanes comprising reacting the butanes in a fluidized bed reactor at a pressure less than about 300 psig with a catalyst composition comprising a crystalline aluminosilicate zeolite having an Alpha Value below about 10.

15. The process according to claim 14 wherein said pressure is less than about 200 psig.

16. The process according to claim 14 wherein the fluidized bed reactor is operated under turbulent conditions at a superficial vapor velocity in the range of about 0.3 to about 2 meters per second.

17. The process according to claim 14 wherein the catalyst is continuously regenerated.

18. The process of claim 14 wherein said process operates at: a temperature in the range of from about 750° to about 1000° F.

19. The process of claim 14 wherein said zeolite has the structure of ZSM-5.

20. The process of claim 14 wherein said Alpha Value is below about 5.

* * * * *